United States Patent [19]
Heath et al.

[11] Patent Number: 5,380,200
[45] Date of Patent: Jan. 10, 1995

[54] ENDODONTIC INSTRUMENT OF PREDETERMINED FLEXIBILITY

[75] Inventors: Derek E. Heath, Johnson City, Tenn.; Carl J. Berendt, Carlsbad, Calif.

[73] Assignee: Quality Dental Products, Inc., Johnson City, Tenn.

[21] Appl. No.: 148,888

[22] Filed: Oct. 8, 1993

[51] Int. Cl.⁶ ............................................. A61C 5/02
[52] U.S. Cl. .................................................... 433/102
[58] Field of Search ................. 433/81, 102, 164, 165, 433/224

[56] References Cited

U.S. PATENT DOCUMENTS

| | | | |
|---|---|---|---|
| 2,797,996 | 7/1957 | Jaffee et al. | 75/175.5 |
| 4,197,643 | 4/1980 | Burstone et al. | 433/20 |
| 4,871,312 | 10/1989 | Heath | 433/164 |
| 4,934,934 | 6/1990 | Arpaio, Jr. et al. | 433/102 |
| 5,017,138 | 5/1991 | Schilder | 433/102 |
| 5,035,618 | 7/1991 | Katz et al. | 433/102 |
| 5,106,298 | 4/1992 | Heath et al. | 433/102 |
| 5,219,284 | 6/1993 | Velvart et al. | 433/102 |

OTHER PUBLICATIONS

"An Initial Investigation of the Bending and Torsional Properties of Nitinol Root Canal Files"; Journal of Endodontics; Jul. 1988; vol. 14, No. 7; pp. 346–351.

"Superelastic Ni–Ti Wire"; Wire Journal International, Mar. 1991; pp. 45–50.

Primary Examiner—Cary E. O'Connor
Assistant Examiner—Nicholas D. Lucchesi
Attorney, Agent, or Firm—Bell, Seltzer, Park & Gibson

[57] ABSTRACT

An endodontic instrument for use in root canal therapy which comprises an inner core of a metal having a specific flexibility, and at least one outer shell of a metal having a different flexibility. By selecting the ratio of the two metals, the instrument may be designed to have a predetermined desired flexibility which is sufficient to assure proper operation of the instrument, yet not so stiff as to risk damage to the tooth canal. A kit which is composed of several such instruments of increasing diameter is also disclosed, and with the instruments being designed to be used sequentially in root canal therapy, and wherein all of the instruments possess substantially the same degree of flexibility. The instruments can thus be used with predictable and consistent results.

22 Claims, 2 Drawing Sheets

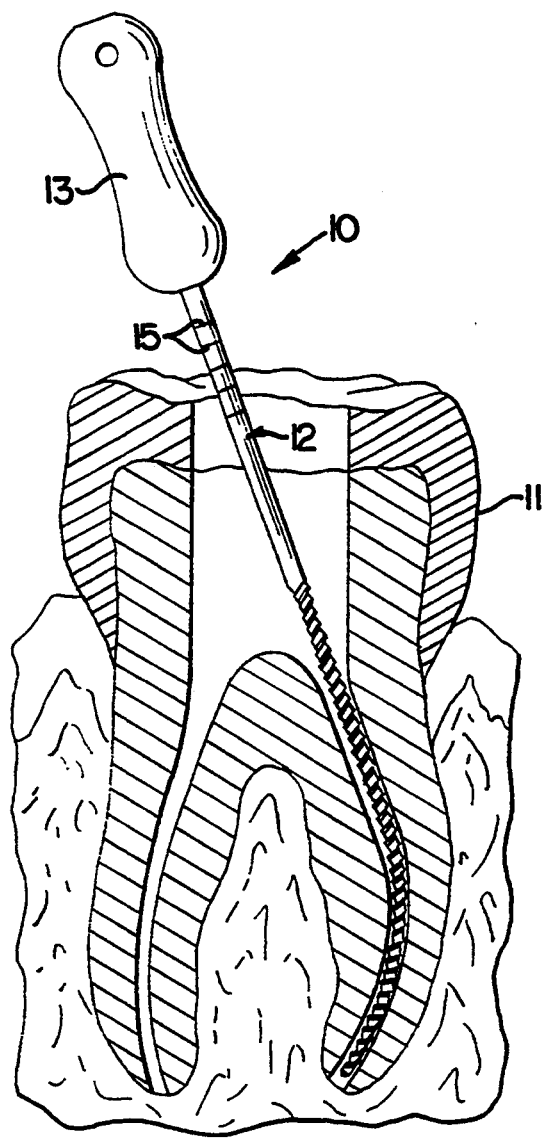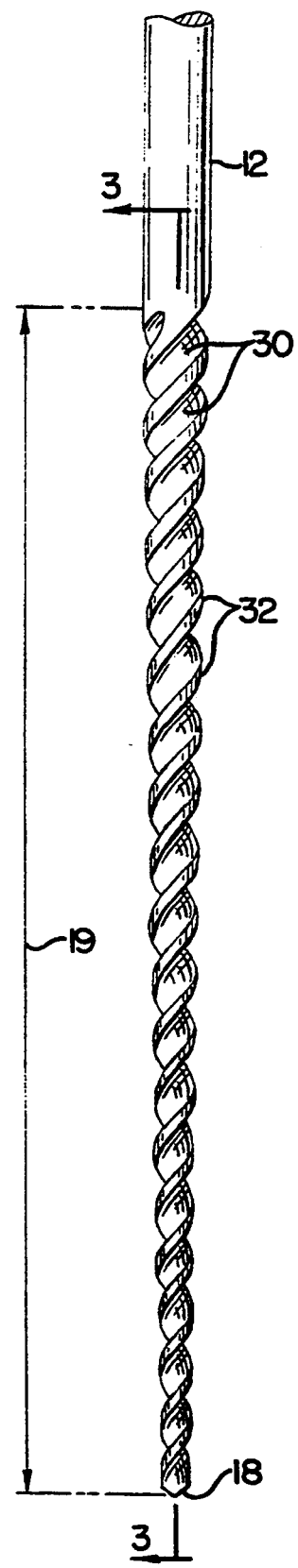
FIG. 1.
FIG. 2.

ENDODONTIC INSTRUMENT OF PREDETERMINED FLEXIBILITY

BACKGROUND OF THE INVENTION

The present invention relates to the field of endodontic instruments adapted for use in performing root canal therapy on teeth, and which are characterized by high flexibility and high resistance to torsional breakage.

Root canal therapy is a well-known procedure wherein the crown of a diseased tooth is opened so as to permit the canal to be cleaned and then filled. More particularly, after opening the crown, a series of very delicate, flexible, finger-held instruments or files are used to clean out and shape the root canal, and each file is manually rotated and reciprocated in the canal by the clinician. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The clinician then fills the tooth above the gutta percha with a protective cement, and lastly, fits a crown to the tooth.

Endodontic files of the described type are commonly supplied to the clinician in kits which comprise several files of increasing diameter. In particular, and in accordance with ANSI/ADA Specification No. 28-1988, files are provided in diameters which range from 0.08 mm at the tip (size 08) to 1.40 mm at the tip (size 140), and the files are provided in kits which contain a number of files of increasing diameter so that the files from a particular kit may be used in sequence by the clinician in accordance with the requirements of the particular canal being cleaned.

As is well-known by clinicians, procedural errors occasionally occur during root canal therapy. These errors result in changes to the root canal morphology such as the perforation of the canal, and the formation of a ledge in the wall of the canal. Also, the instrument may fracture. These errors usually occur because the endodontic instruments, which are typically formed of stainless steel, lack the requisite flexibility particularly in the larger diameter instruments. Thus, upon being inserted into the root canal of a tooth, the stainless steel instrument is often unable to conform to the sometimes compound curvature or outline of the canal. In particular, the instrument tends to cut into the inside edges of the curved canal (referred to as transportation), which can lead to the perforation of the wall of the canal, and ledges may be formed at the pilot end of the instrument by reason of a lateral movement of the pilot end.

Depending upon the severity of these errors, repair measures might be needed. For instance, if a perforation of the wall results, the perforation must be repaired to prevent bacteria from collecting and the possibility of saliva leaking into the cavity.

Recently, endodontic files composed of a nickel-titanium alloy have been introduced, which provide a high degree of flexibility in both bending and torsion, and superior resistance to fracture, as compared to stainless steel instruments. In this regard, reference is made to the article entitled "An Initial Investigation of the Bending and the Torsional Properties of Nitinol Root Canal Files", *Journal of Endodontics,* Volume 14, No. 7, July 1988, at pages 346-351.

While the new nickel-titanium instruments have been found to reduce transportation and the formation of ledges in the canal, in the smaller sizes, the highly flexible nature of the instruments reduces their filing or cleaning efficiency. Also, the tips of the instruments tend to deflect back upon themselves in severely curved canals.

It is accordingly an object of the present invention to provide an endodontic instrument which has a predetermined desired degree of flexibility for a given size or diameter of the instrument.

It is a further object of the present invention to provide a kit comprising a plurality of endodontic instruments wherein each instrument in the kit exhibits a predetermined desired degree of flexibility, and with the flexibilities of the instruments being chosen so as to provide an effective and predictable operational result for each of the instruments in the kit.

It is a more particular object of the present invention to provide a kit of a plurality of endodontic instruments of progressively increasing diameter, and wherein the instruments of smaller diameter have sufficient stiffness for effective filing and cleaning of the canal, and the instruments of larger diameter have sufficient flexibility to minimize transportation and ledge formations.

SUMMARY OF THE INVENTION

The above and other objects and advantages of the present invention are achieved in the embodiment illustrated herein by the provision of an endodontic instrument which comprises an elongate shank having a proximate end and an opposite pilot end and so as to define a working length adjacent said pilot end. At least one continuous helical flute is formed in the shank so as to extend along the working length, and the shank comprises a core of a first material, and at least one outer shell coaxially surrounding the core and comprising a second material. The first and second materials in the shank have differing flexibilities such that the relative amounts of said first and second materials define a predetermined desired flexibility for the shank.

Preferably, the first and second materials are each metallic, and in one embodiment the first metallic material is nickel-titanium alloy, and the second material is selected from the group consisting of stainless steel, titanium alpha alloy, titanium beta alloy, and titanium alpha beta alloy. In another embodiment, each of the first and second materials is selected from the group consisting of pure titanium, nickel-titanium alloy, and niobium-titanium alloy.

Instruments of the above construction may be provided in a kit, with the instruments in the kit having progressively increasing diameters. Also, the shanks of the instruments are composed of the first and second metallic materials which are selected and configured so that the shanks of all of the instruments have a predetermined desired flexibility. In the preferred embodiment, the flexibility of all of the instruments in the kit is between about 80 and 375 gm. cm., and the flexibility is substantially the same for all of the instruments in the kit. Also, the flexibility may vary from kit to kit, so that the clinician can easily predict the performance of each instrument with respect to a given root canal configuration, and as a result, the performance of effective, skilled root canal therapy is enhanced.

The kit of instruments of the present invention is provided, in the most preferred embodiment, with a plurality of instruments in conventional sizes as set forth in the above referenced ANSI/ADA specifications. That is, endodontic files are typically provided in kits with increasing working length diameters to precisely perform various therapies. The consistent and known flexibility of the individual instruments within the kit is maintained by proportioning the ratio of the more flexible component with respect to the more stiff component. Smaller instruments require a greater amount of the more stiff component in proportion to the more flexible component while larger instruments would require a greater proportion of the more flexible component.

BRIEF DESCRIPTION OF THE DRAWINGS

Some of the objects and advantages of the present invention having been stated, others will appear as the description proceeds, when taken in conjunction with the accompanying drawings, in which FIG. 1 is a sectional side elevation view of a tooth undergoing root canal therapy, utilizing an endodontic instrument in accordance with the present invention;

FIG. 2 is a side elevation view of the shank of the instrument shown in FIG. 1;

DETAILED DESCRIPTION OF THE DRAWINGS

Figure 3:
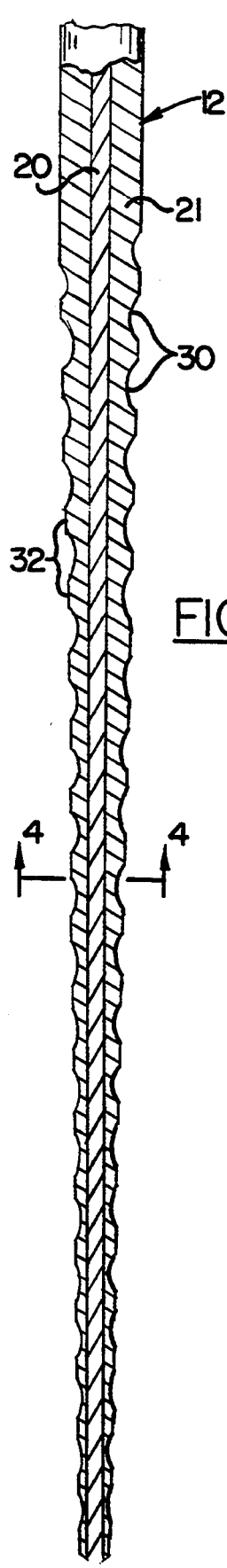
FIG. 3 is a longitudinal sectional view of the shank of the instrument.

Referring more particularly to the drawings wherein like numerals reference like parts, an endodontic instrument or file which embodies the features of the present invention is indicated generally at 10, and in FIG. 1 the file is illustrated in an operative position in a typical root canal in a tooth 11. The file 10 comprises a shank 12 which is composed of a composite metal as further described below, and which typically has a length of about 30 mm. The shank 12 also includes an outer or proximate end which mounts a conventional handle 13. The portion of the shank immediately below the handle is cylindrical and has a diameter of between about 0.5 and 1.6 mm, and this shank portion includes calibrated depth markings 15 of conventional design. The shank further includes an opposite distal or pilot end 18, shown best in FIG. 2, and a working length 19 which is defined adjacent the pilot end 18. The working length may be cylindrical (not shown), or as illustrated it may be slightly tapered toward the pilot end 18 at an included angle of between about one half and four degrees.

As best seen in FIG. 3, the shank 12 comprises a cylindrical core 20 of a first metallic material, and an outer shell 21 coaxially surrounding the core and which is composed of a second metallic material. The first material of the core 20 and the second material of the outer shell 21 have differing flexibilities, and such that relative amounts of the first and second materials define a predetermined desired flexibility for the shank.

In one preferred embodiment, the first metallic material of the core 20 has a relatively high flexibility, and it is composed of nickel-titanium alloy which has a very low modulus of elasticity, only one-fourth to one-fifth the value for stainless steel, and a very wide range of elastic deformation. Most preferably "55-Nitinol" alloy is used for the core material which contains 54–56 weight percent nickel with the balance comprising titanium. This alloy possesses unique mechanical memory, is non-magnetic, is corrosion resistant and has a relatively low density of 0.234 lb. per cu. in.

The second metallic material of the outer shell 21 has a relatively low flexibility and may comprise for example stainless steel, titanium alpha alloy, titanium beta alloy, and titanium alpha beta alloy. The compositions of the three above noted titanium alloys are well known, and a further definition may be obtained from U.S. Pat. No. 4,197,643 and 2,797,996, the disclosures of which are incorporated herein by reference. Also, the following represent a specific example of each of the alloys:

(a) Titanium alpha alloy: Titanium alloy with 5% aluminum and 2.5% tin.

(b) Titanium beta alloy: Titanium alloy with 13% vanadium, 11% chromium, and 3% aluminum.

(c) Titanium alpha beta alloy: Titanium alloy with 6% aluminum, 2% tin, 4% zirconium, and 2% molybdenum.

In accordance with the present invention, the proportion of the first and second materials may be varied to permit the file 10 to possess a predetermined desired flexibility. Thus for example, the percentage of the material of the core 20 is reduced for the small diameter files to impart more stiffness, whereby the percentage of the material of the core is increased for the larger diameter files to impart more flexibility.

In another preferred embodiment of the invention, each of the first and second materials is selected from the group consisting of pure titanium, nickel-titanium alloy, and niobium-titanium alloy. The nickel-titanium alloy preferably comprises "55-Nitinol" alloy as described above, and the niobium-titanium alloy preferably comprises between about 40 to 50% niobium and the balance titanium. These materials may be selected and configured so as to provide a desired flexibility to the instrument. The following are specific examples of several suitable configurations:

1) A core of pure titanium and an outer shell of nickel-titanium alloy.

2) A core of niobium-titanium alloy and an outer shell of nickel-titanium alloy.

3) A core of pure titanium, a first outer shell of nickel-titanium alloy, and a second outermost shell of niobium-titanium alloy.

4) A core of niobium-titanium alloy, a first outer shell of nickel-titanium alloy, and a second outermost shell of niobium-titanium alloy.

Figure 4:
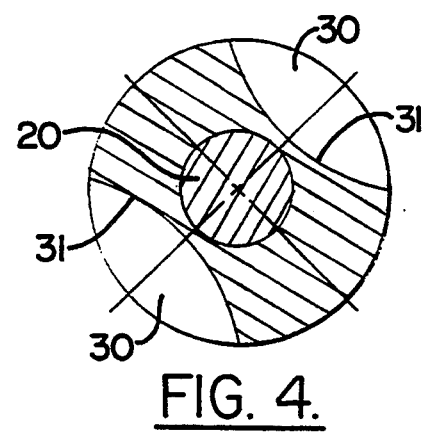
FIG. 4 is a transverse sectional view of the shank of the instrument.

In the illustrated embodiments, the working length 19 of the instrument is tapered toward the pilot end at an included angle of between about ½ and 4 degrees. Preferably, and in accordance with the above identified ANSI/ADA Specification, the taper is 0.02 mm difference in diameter per millimeter of the working length. Also, the working length 19 further comprises two continuous helical flutes 30 which extend along its length. The flutes are preferably machined in the outer surface of the outer shell material in the manner further described in U.S. Pat. No. 4,934,934. This machining operation may result in a cross section as seen in FIG. 4. More particularly, each of the two flutes 30 defines a curved concave wall 31 when viewed in transverse cross section, and a helical land 32 is positioned between axially adjacent flute sections. Alternatively, a machining operation may be employed which produces a triangular or quadrangular cross section (not shown).

Figure 5:
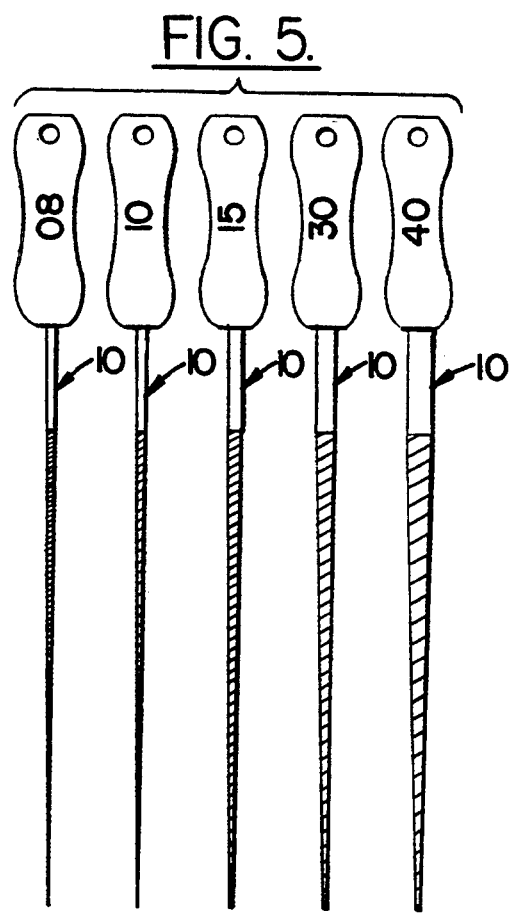
FIG. 5 is a side elevational view of a kit of instruments in accordance with the present invention.

The instruments of the present invention may be provided in kits, which facilitate their use by the clinician. In particular, the kit comprises a plurality of several instruments 10 as schematically illustrated in FIG. 5, and which are adapted to be serially used in performing root canal therapy. The shanks of the instruments in the kit have progressively increasing diameters, as indicated by the size designations printed on the handles 13. Also, the shanks 12 having different proportions of the first and second materials so that all of the instruments have a predetermined desired flexibility. Preferably, the shanks are designed so that the flexibility of all of the shanks in the kit is substantially the same.

The term "flexibility" as used herein refers to the "stiffness" as defined in the above referenced ANSI/ADS Specification. As there defined, the flexibility or stiffness is determined by holding the instrument in a torque meter, bending the shank at an angle of 45°, and then measuring the required torque. With the present invention, the flexibility of the shanks of all of the instruments in the kit is preferably between about 80 and 375 gm. cm.

As noted above, the flexibility of all of the instruments in a kit may be substantially the same. However, the flexibility from kit to kit may vary, so that the clinician may select a kit with a particular flexibility to best meet the needs of the canal being processed. For example, in the case of a highly curved canal, a kit of instruments of relatively high flexibility would be selected, whereas in the case of a relatively straight canal, a more stiff kit would be selected.

The instrument 10 is fabricated by a process wherein a bar of the material of the outer shell 21 is provided which has a diameter of several inches, e.g. 4 to 6 inches. The bar is through bored, and a rod of the core 20 material is fitted within the bore in a close fitting relationship. Next, the composite member is rolled or drawn to the desired final diameter by the same process presently used to produce finished wire. Thereafter, the portion of the composite member which is to form the working length of the instrument may be tapered by a suitable grinding operation, and the flutes 30 are then ground in the tapered surface. In this regard, it will be understood that the radial thickness of the outer shell 21 should be sufficient to receive the full depth of the flutes 30. Finally, the handle 13 is assembled in a conventional manner.

In the case of instruments having more than one outer shell, a bar of the material of the outermost shell is bored to coaxially receive a previously bored sleeve of the material of the inner shell, and a rod of the material of the core is fitted within the sleeve. The composite member is then rolled or drawn to the desired final diameter in the manner described above.

In the drawings and specification, there has been set forth preferred embodiments of the invention, and although specific terms are employed, they are used in a generic and descriptive sense only and not for purposes of limitation.

That which is claimed is:

1. An endodontic instrument which is adapted for use in performing root canal therapy, and comprising
    an elongate shank having a proximate end and an opposite pilot end, and at least one continuous helical flute formed in said shank so as to extend along at least a major portion of the axial length of said shank and to said pilot end and so as to define a working length of said shank,
    said shank comprising a core of a first material, and at least one outer shell coaxially surrounding said core and extending along the entire working length of said shank and comprising a metallic second material, and with said first and second materials having differing flexibilities and such that the relative amounts of said first and second materials define a predetermined desired flexibility for the shank.

2. The endodontic instrument as defined in claim 1 wherein one of said first and second materials is nickel-titanium alloy.

3. The endodontic instrument as defined in claim 2 wherein said nickel-titanium alloy is between 54 to 56 weight percent nickel and the balance titanium.

4. The endodontic instrument as defined in claim 2 wherein the other of said first and second materials is selected from the group consisting of stainless steel, titanium alpha alloy, titanium beta alloy, and titanium alpha beta alloy.

5. The endodontic instrument as defined in claim 1 wherein said first and second materials are each metallic, and wherein said first metallic material has a relatively high flexibility and said second metallic material has a relatively low flexibility.

6. The endodontic instrument as defined in claim 5 wherein said first metallic material is nickel-titanium alloy and wherein said second metallic material is selected from the group consisting of stainless steel, titanium alpha alloy, titanium beta alloy, and titanium alpha beta alloy.

7. The endodontic instrument as defined in claim 1 wherein said shank has a predetermined flexibility of between about 80 and 375 gm. cm.

8. The endodontic instrument as defined in claim 1 wherein said working length of said shank includes a peripheral surface which is tapered toward said pilot end at an included angle of between about ½ and 4 degrees.

9. The endodontic instrument as defined in claim 1 further comprising a handle mounted at said proximate end of said shank.

10. The endodontic instrument as defined in claim 1 wherein said at least one flute defines a curved concave wall when viewed in transverse cross section, and wherein a helical land is positioned between axially adjacent flute segments.

11. A kit comprising a plurality of endodontic instruments which are adapted for use in performing root canal therapy, with each of said instruments comprising an elongate shank having a proximate end and an opposite pilot end and so as to define a working length adjacent said pilot end, and at least one continuous helical flute formed in said shank so as to extend along said working length,
    said shanks of at least a plurality of said instruments of said kit each comprising a core of a first metallic material, and at least one outer shell coaxially surrounding the entire length of said core and comprising a second metallic material, and said shanks of said instruments respectively having progressively increasing diameters, with the composition of the first and second metallic materials being selected and the configuration of said shanks being configured so that the shanks of all of said instruments have a predetermined desired flexibility.

12. The kit as defined in claim 11 wherein one of said first and second metallic materials is nickel-titanium alloy.

13. The kit as defined in claim 12 wherein the flexibility of said shanks of all of said instruments is between about 80 and 375 gm. cm.

14. The kit as defined in claim 13 wherein the flexibility of said shanks of all of said instruments is substantially the same.

15. The kit as defined in claim 12 wherein said working length of said shank of each of said instruments includes a peripheral surface which is tapered toward the associated pilot end at an included angle of between about ½ and 4 degrees.

16. The kit as defined in claim 15 wherein each of said instruments further comprises a handle mounted at said proximate end of the associated shank.

17. The kit as defined in claim 12 wherein said at least one flute of each of said instruments defines a curved concave wall when viewed in transverse cross section, and wherein a helical land is positioned between axially adjacent flute segments of each of said instruments.

18. The kit as defined in claim 12 wherein said first metallic material is nickel-titanium alloy.

19. The kit as defined in claim 18 wherein said second metallic material is selected from the group consisting of stainless steel, titanium alpha alloy, titanium beta alloy, and titanium alpha beta alloy.

20. The kit as defined in claim 12 wherein each of said first and second materials is selected from the group consisting of titanium, nickel-titanium alloy, and niobium-titanium alloy.

21. An endodontic instrument which is adapted for use in performing root canal therapy, and comprising
an elongate shank having a proximate end and an opposite pilot end and so as to define a working length adjacent said pilot end, and at least one continuous helical flute formed in said shank so as to extend along said working length,
said shank comprising a core of a first material, and at least one outer shell coaxially surrounding said core and comprising a second material, said first and second materials in said shank having differing flexibilities such that the relative amounts of said first and second materials define a predetermined desired flexibility for the shank, one of said first and second materials being selected from the group consisting of stainless steel, titanium alpha alloy, titanium beta alloy, and titanium alpha beta alloy, and the other of said first and second materials being nickel-titanium alloy.

22. An endodontic instrument which is adapted for use in performing root canal therapy, and comprising
an elongate shank having a proximate end and an opposite pilot end and so as to define a working length adjacent said pilot end, and at least one continuous helical flute formed in said shank so as to extend along said working length,
said shank comprising a core of a first material, and at least one outer shell coaxially surrounding said core and comprising a second material, said first and second materials in said shank having differing flexibilities such that the relative amounts of said first and second materials define a predetermined desired flexibility for the shank, each of said first and second materials being selected from the group consisting of titanium, nickel-titanium alloy, and niobium-titanium alloy.

* * * * *